US009861796B2

(12) United States Patent
Osumi et al.

(10) Patent No.: US 9,861,796 B2
(45) Date of Patent: Jan. 9, 2018

(54) PRODUCTION METHOD FOR EXPANSION BALLOON

(71) Applicant: KANEKA CORPORATION, Osaka-shi, Osaka (JP)

(72) Inventors: Shintaro Osumi, Settsu (JP); Yoichi Yamaguchi, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 523 days.

(21) Appl. No.: 14/367,091

(22) PCT Filed: Dec. 14, 2012

(86) PCT No.: PCT/JP2012/082543
§ 371 (c)(1),
(2) Date: Jun. 19, 2014

(87) PCT Pub. No.: WO2013/094541
PCT Pub. Date: Jun. 27, 2013

(65) Prior Publication Data
US 2015/0021834 A1   Jan. 22, 2015

(30) Foreign Application Priority Data
Dec. 20, 2011   (JP) .................. 2011-279010

(51) Int. Cl.
A61M 25/10       (2013.01)
B29C 49/08       (2006.01)
(Continued)

(52) U.S. Cl.
CPC .............. *A61M 25/1029* (2013.01); *A61M 2025/1084* (2013.01); *B29C 49/04* (2013.01);
(Continued)

(58) Field of Classification Search
None
See application file for complete search history.

(56) References Cited

U.S. PATENT DOCUMENTS

2008/0171977 A1* 7/2008 Blix .................. A61M 25/10
604/96.01

FOREIGN PATENT DOCUMENTS

EP   0 414 350 A1   2/1991
JP   3-92173 A      4/1991
(Continued)

OTHER PUBLICATIONS

International Search Report, issued in PCT/JP2012/082543, dated Mar. 12, 2013.

*Primary Examiner* — Monica Huson
(74) *Attorney, Agent, or Firm* — Birch, Stewart, Kolasch & Birch, LLP

(57) ABSTRACT

The present invention is a production method for an expansion balloon (2) for use in a balloon catheter (1), including the steps of; forming a balloon tube (8) by extrusion molding so as to have a cross section orthogonal to an axial direction with the shape of a circle on the outside and the shape of a polygon having a circumcircle on the inside; and placing the balloon tube (8) in a mold to perform biaxially-stretched blow molding to obtain the balloon, whereby it is possible to produce the expansion balloon (2) that has no unevenness in film thickness of a straight pipe part (4) and allows stable folding control by simple processes with favorable molding yields.

6 Claims, 4 Drawing Sheets

(51) Int. Cl.
    *B29K 77/00*     (2006.01)
    *B29K 105/00*     (2006.01)
    *B29L 31/00*     (2006.01)
    *B29C 49/04*     (2006.01)
    *B29C 71/02*     (2006.01)

(52) U.S. Cl.
    CPC ........ *B29C 49/08* (2013.01); *B29C 2071/022* (2013.01); *B29K 2077/00* (2013.01); *B29K 2105/258* (2013.01); *B29K 2995/0053* (2013.01); *B29L 2031/7543* (2013.01)

(56) References Cited

FOREIGN PATENT DOCUMENTS

| | | |
|---|---|---|
| JP | 6-506848 A | 8/1994 |
| JP | 2003-62080 A | 3/2003 |
| JP | 2007-157 A | 1/2007 |
| JP | 2010-506655 A | 3/2010 |
| WO | WO 92/19306 A1 | 11/1992 |
| WO | WO 2008/051337 A2 | 5/2008 |

\* cited by examiner

[Fig. 1]
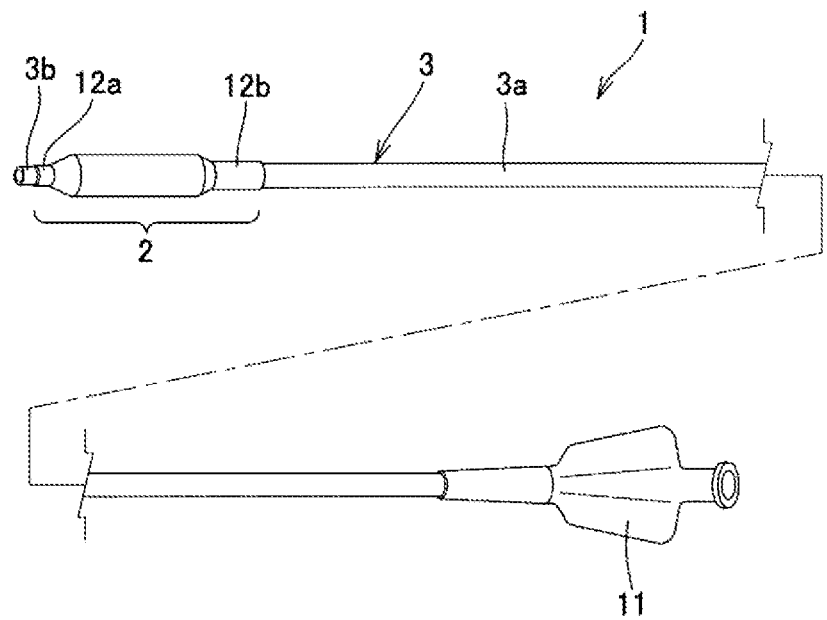
[Fig. 2]
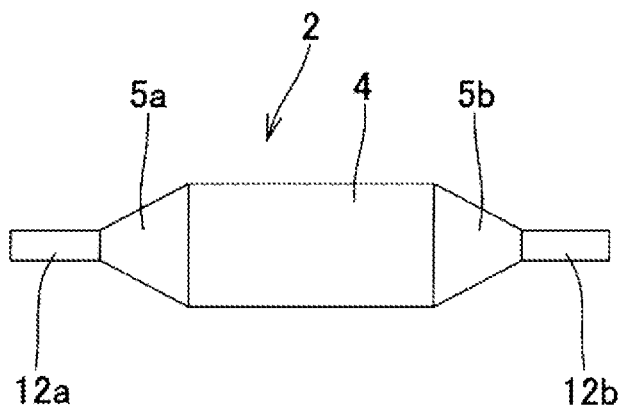
[Fig. 3]
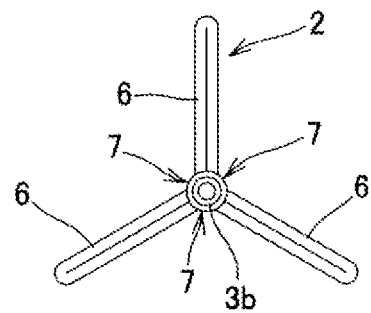

[Fig. 4]
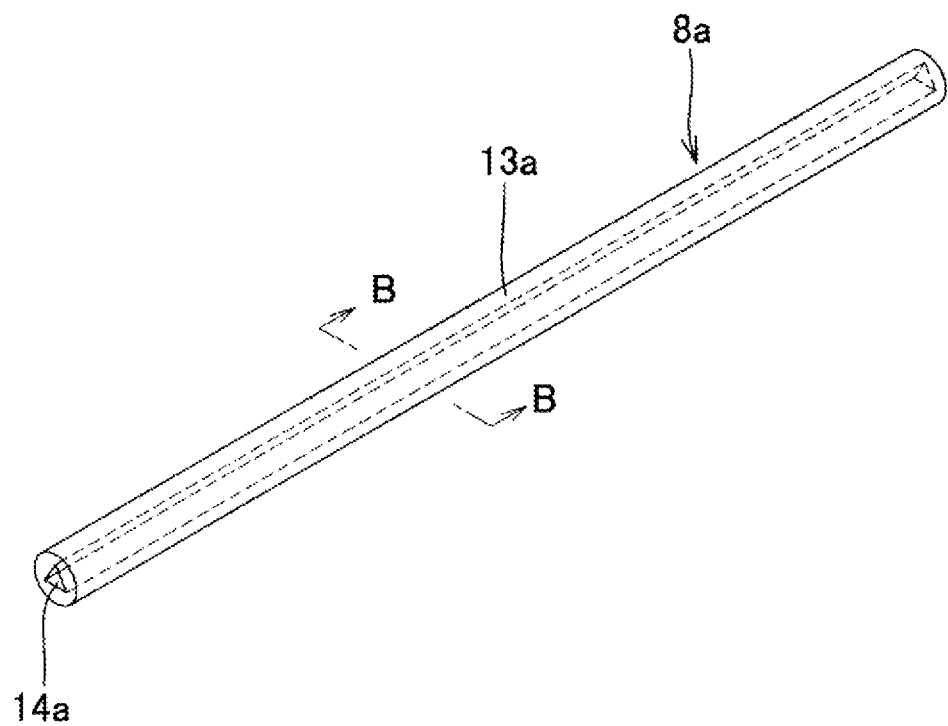

[Fig. 5]
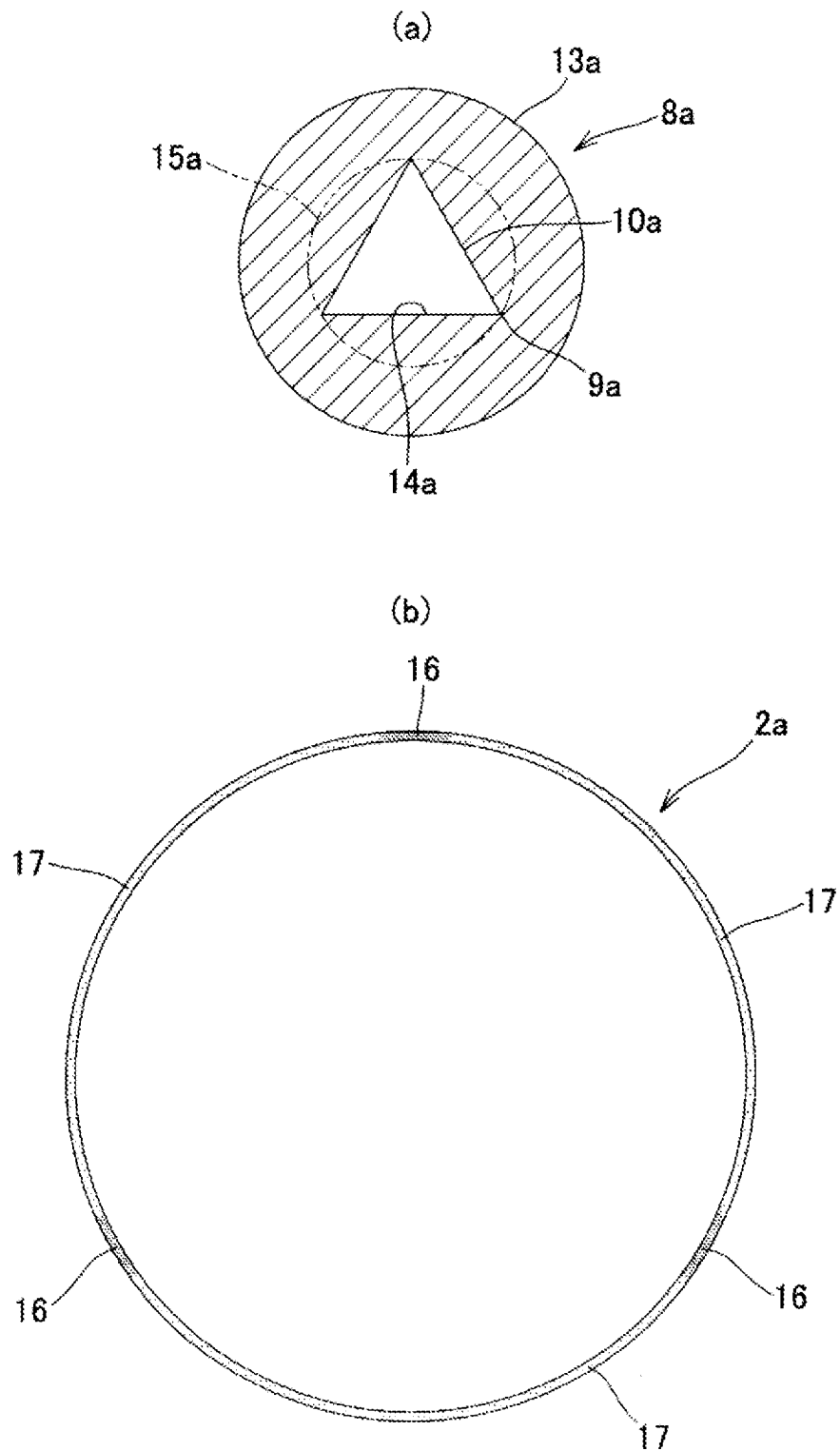

[Fig. 6]
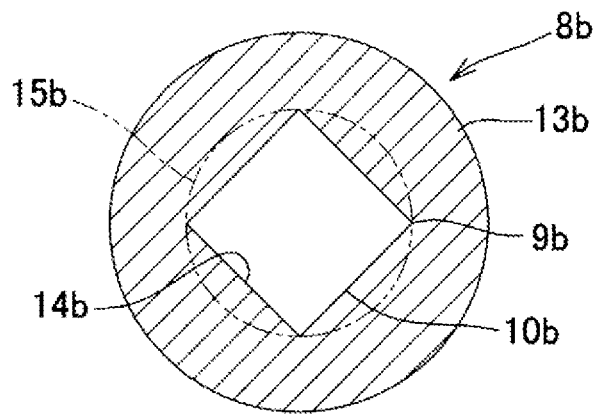
[Fig. 7]
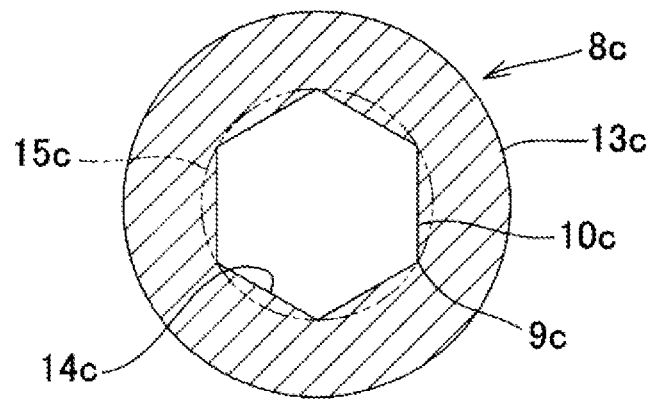
[Fig. 8]
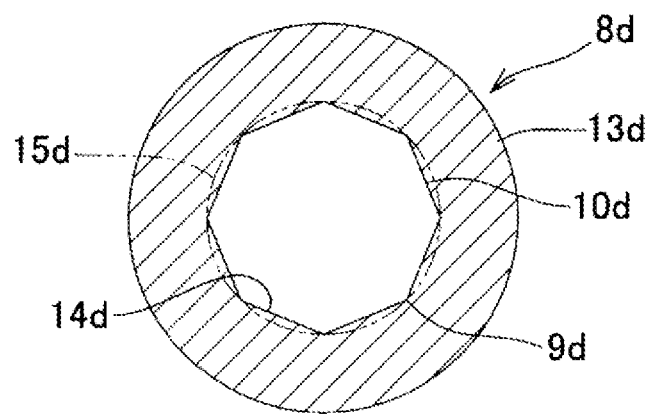

PRODUCTION METHOD FOR EXPANSION BALLOON

TECHNICAL FIELD

The present invention relates to a production method for an expansion balloon, more specifically, a production method for an expansion balloon for use in a balloon catheter that performs dilation treatment on a narrowed area of a blood vessel to restore a blood flow at percutaneous luminal surgery including peripheral angioplasty, coronary artery angioplasty, and valvuloplasty.

BACKGROUND ART

Conventionally, percutaneous angioplasty is widely utilized in dilation treatment for narrowed area, an occluded area, and the like of a vascular lumen to restore or improve a blood flow in coronary artery, peripheral blood vessel, and the like. The balloon catheter for use in percutaneous angioplasty is generally structured such that an expansion balloon capable of inflation and contraction by adjusting an internal pressure is joined to a leading end of a shaft, and a lumen into which a guide wire is inserted (guide wire lumen) and a lumen that supplies a pressure fluid for adjustment of a balloon internal pressure (inflation lumen) are provided in the inside of the shaft along the longitudinal direction of the shaft.

A general example of PTCA (percutaneous transluminal coronary angioplasty) using such a balloon catheter is as described below.

First, the guide catheter is inserted from a puncture site in a femoral artery, a brachial artery, a radial artery, or the like, and a leading end of the guide catheter is positioned at the entrance of a coronary artery through a main artery. Then, the guide wire inserted into the guide wire lumen is advanced beyond the narrowed area in the coronary artery, and the balloon catheter is inserted along the guide wire and the position of the balloon is aligned with the narrowed area. Then, a device such as an indeflator is used to supply a pressure fluid to the balloon through the inflation lumen and inflate the balloon for dilation treatment of the narrowed area.

If there exists a plurality of narrowed areas in the lumens of the body, the expansion balloon may be inflated and then contracted at one site and then is passed through another site (re-cross) for expansion of the narrowed area.

The expansion balloon is structured by a columnar straight pipe part and tapered conical ends of the same. When the inflated balloon is contracted again, the straight pipe part and the taper parts of the balloon have wing parts and groove parts formed alternately, which constitutes a folding shape extended from the leading end to the base end of the balloon in the longitudinal direction. At that time, there may arise a flat phenomenon that a pair of opposed wing parts is extended in a radial direction, that is, a winging shape with the two wing parts. It is difficult to insert the thus shaped balloon into the narrowed area. Therefore, when being folded, the balloon is desirably shaped to have a large number of wing parts (three or more). Accordingly, the dimension of the balloon becomes shorter in the radial direction, which reduces a profile diameter of the balloon when being folded and facilitates passage of the balloon. To that end, various folding methods of balloon have been suggested.

For example, Patent Document 1 discloses a method for controlling folding of a balloon by which the cross section of the balloon is provided with film thickness distribution and the balloon folding is controlled by a difference in rigidity between a thin part and a thick part. However, when the balloon cross section is provided with film thickness distribution to ensure pressure capacity of the balloon, the film thickness of the thin part in the balloon tube is set according to the pressure capacity required for the balloon. Thus, it is inevitable that the thick part of the balloon tube becomes excessively thick, and as a result, the balloon becomes thick as a whole and the profile diameter of the balloon when being folded becomes larger. To make the entire balloon thin, it is necessary to reduce the film thickness of the thick part in the balloon, and in this case, it is not possible to ensure pressure capacity as stated above.

Meanwhile, besides initial passage of the balloon part through a narrowed area, it is important to, after expansion of the balloon, ensure passage (re-cross) of the balloon inserted into the same again or another narrowed area. It cannot be said that the balloon described in Patent Document 1 is high in insertion operability as a catheter because the initial passage of the balloon through a narrowed area is deteriorated. In addition, since there are large variations in film thickness of the balloon, there is a major problem that it is difficult to stably control folding of the balloon, which deteriorates re-cross capability. Further, it is necessary to provide the balloon tube with an excessive thickness difference before blow molding, which makes it very difficult to produce the balloon tube and the balloon using the balloon tube, thereby leading to reduction in molding yield.

In addition, Patent Document 2 discloses a method for controlling folding of a balloon by which a balloon tube having ribs formed by extrusion molding is used to provide the balloon with at least three ribs (grooves) on the inner surface thereof (in a thickness direction). However, as with the method described in Patent Document 1, the film thickness of a thinner rib part of the balloon tube is set according to pressure capacity required for the balloon, and thus the film thickness of the thicker side of the balloon becomes large excessively. As a result, the entire balloon becomes thick and the profile diameter of the balloon when being folded becomes large, which leads to a major problem that the balloon deteriorates in initial passage through a narrowed area and re-cross capability.

In addition, Patent Document 3 discloses a method for controlling folding of a balloon by which a mold is shaped in advance to have a plurality of longitudinal grooves continued at least in a long-axis direction and wing parts equal in number to the longitudinal grooves and corresponding to the longitudinal grooves, and a balloon is provided with the wing parts and the longitudinal grooves corresponding to a scroll-shaped cross section formed by concave grooves and convex streaks. As in the invention of Patent Document 3, forming the wing parts and the longitudinal grooves makes it possible to realize the balloon's stable folding tendency. However, if the balloon is shaped to realize a stable folding tendency, there is a problem that, when being expanded, the shape of the balloon does not become almost circular, and thus the thus shaped balloon cannot be used in clinical practice. In addition, the mold used for shaping the balloon has a very complicated shape, which results in waste of a large amount of time for product development and excessive increase of production costs. In these regards, there is still room for improvement in the invention of Patent Document 3.

CITATION LIST

Patent Literatures

Patent Document 1: JP-A No. H 03-92173
Patent Document 2: JP-T No. H 06-506848
Patent Document 3: JP-A No. 2003-62080

SUMMARY OF INVENTION

Technical Problem

To solve the foregoing problems, an object of the present invention is to provide a production method of an expansion balloon for use in a balloon catheter that has no unevenness in film thickness of the balloon, and allows stable control on folding of the balloon. Another object of the present invention is to provide a production method for an expansion balloon that has simple processes for balloon production from a balloon tube and provides favorable molding yields of the balloon tube and the balloon.

Solution to Problem

To solve the foregoing problems, the inventors of the present invention have earnestly conducted studies and then found that, when a balloon is obtained by performing biaxially-stretched blow molding on a balloon tube having a cross section with the shape of a circle on the outside and the shape of a polygon on the inside, the balloon has no unevenness in film thickness at the straight pipe part and the balloon allows folding control, thereby completing the present invention.

Specifically, the present invention is a production method for an expansion balloon for use in a balloon catheter, including the steps of; obtaining a balloon tube that has a cross section orthogonal to an axial direction with the shape of a circle on the outside and the shape of a polygon having a circumcircle on the inside; and placing the balloon tube in a mold for biaxially-stretched blow molding to obtain the balloon.

The present invention also relates to the production method for an expansion balloon, wherein the balloon tube has the cross section with the shape of a circle on the outside and the shape of a polygon having a circumcircle in multiples of 3 or 4 on the inside.

The present invention also relates to the production method for an expansion balloon, wherein the balloon tube has the cross section with the shape of a circle on the outside and the shape of a polygon having any circumcircle selected from among a tetragon, a hexagon, and an octagon on the inside.

The present invention also relates to the production method for an expansion balloon, wherein the polygon having a circumcircle is a regular polygon.

The present invention also relates to the production method for an expansion balloon, wherein the outside shape and inside shape of the cross section of the balloon tube are formed over the entire length in the axial direction.

The present invention also relates to the production method for an expansion balloon, wherein the balloon has a straight pipe part and film thickness of the straight pipe part is almost uniform.

The present invention also relates to the production method for an expansion balloon, wherein expansion rate of the balloon under the biaxially-stretched blow molding is 4 or more and 9 or less.

Advantageous Effects of Invention

According to the production method of the present invention, it is possible to provide a balloon in which the film thickness of the straight pipe part is almost uniform and stable folding control is allowed. In addition, the balloon obtained by the production method of the present invention can be smaller in profile diameter when the balloon is folded. According to the present invention, the process for producing a balloon from a balloon tube is simple and the molding yields of the balloon tube and the balloon are high, which makes it possible to produce the balloon at low cost.

BRIEF DESCRIPTION OF THE DRAWINGS

FIG. 1 is an overall schematic view of a general balloon catheter;
FIG. 2 is a side view of an outer structure of a general expansion balloon;
FIG. 3 is a schematic front view of the expansion balloon in a folded state;
FIG. 4 is a schematic perspective view of a first embodiment of a balloon tube for use in the present invention;
FIG. 5($a$) is a cross-sectional view of FIG. 4 taken along B-B line, and FIG. 5($b$) is an illustrative diagram of a cross section of a straight pipe part of an expansion balloon obtained by subjecting the balloon tube shown in FIG. 4 to biaxially-stretched blow molding;
FIG. 6 is a cross-sectional view of a second embodiment of a balloon tube for use in the present invention;
FIG. 7 is a cross-sectional view of a third embodiment of a balloon tube for use in the present invention; and
FIG. 8 is a cross-sectional view of a fourth embodiment of a balloon tube for use in the present invention;

DESCRIPTION OF EMBODIMENTS

Embodiments of the present invention will be described below with reference to FIGS. 1 to 6. The embodiments shown in these drawings are intended for more specific illustration of the present invention, and the present invention is not limited to the embodiments shown in these drawings.

There is no particular limitation on material for an expansion balloon for use in the present invention. For example, the material may be a polymer material such as polyurethane, polyethylene, polypropylene, polyester, polyamide, polyurethane elastomer, or polyamide elastomer. Alternatively, the material may be a blended material in which two or more of the foregoing polymer materials are mixed. In addition, there is no particular limitation on hardness of material for the balloon, but from the viewpoint of realization of a stable folding tendency, Shore hardness is preferably 55D to 74D. Material having a Shore hardness within this range allows shaping of the expansion balloon without great difficulty. The expansion balloon produced from a material with a Shore hardness of less than 55D tends to exhibit rubber property, and the expansion balloon produced from a material with a Shore hardness of more than 74D tends to be hard and less prone to expand.

FIG. 1 is an overall schematic view of a general balloon catheter. The expansion balloon obtained by the production method of the present invention is used for such a balloon catheter, for example. The balloon catheter 1 shown in FIG. 1 includes an expansion balloon 2, a catheter shaft 3 extending in a long-axis direction, and a hub 11. The expansion balloon 2 is disposed at a distal part of the balloon catheter 1, and the hub 11 is disposed at a proximal part of the balloon catheter 1. The catheter shaft 3 has a double-pipe structure, and is formed from an outer pipe 3a that is joined to a proximal part of the expansion balloon 2 and extended to the proximal part, and an inner pipe 3b that is disposed at an inner cavity part of the outer pipe 3a and is extended from the proximal side to the distal side through the inner cavity part of the expansion balloon 2. Although not shown in this drawing, the balloon catheter 1 is a rapid-exchange balloon catheter in which a proximal end of the inner pipe 3b forms an opening part penetrating through a side wall of the outer pipe 3a. The inner pipe 3b has an inner cavity part that communicates from a distal end part to a proximal end part so that a guide wire can be inserted into and passed through the inner cavity part. The outer pipe 3a has an inner cavity part that communicates from a distal end part to a proximal end part, and the inner cavity part allows the outer pipe 3a to communicate with the outside via the hub 11 from the inner cavity part of the expansion balloon 2. The balloon catheter 1 is not limited to the rapid-exchange balloon catheter, but may be an over-the-wire balloon catheter in which the inner pipe extends over the entire length of the outer pipe, or may include a catheter shaft that does not have a double-pipe structure.

FIG. 2 is a diagram showing an outer structure of a general expansion balloon, and the expansion balloon 2 is formed from a straight pipe part 4 with a columnar outer shape, conical tapers (5a on the distal side and 5b on the proximal side) at both ends of the straight pipe part 4, and columnar sleeve parts (12a on the distal side and 12b on the proximal side) continued from the conical tapers 5. In this drawing, the expansion balloon 2 is joined at the distal-side sleeve part 12a to the distal side of the inner pipe 3b shown in FIG. 1, and is joined at the proximal-side sleeve part 12b to the distal side of the outer pipe 3a. Thus, the inner and outer diameters of the distal-side sleeve part 12a are smaller than inner and outer diameters of the proximal-side sleeve part 12b, but this relationship can be changed as appropriate depending on the structure of the balloon catheter. In addition, the inner and outer diameters of the straight pipe part, the taper angle of the taper parts, and the like can be changed as appropriate depending on the usage of the balloon catheter and the like.

When the expansion balloon 2 is used to assemble the balloon catheter 1 shown in FIG. 1, for example, and the expansion balloon 2 is expanded and then contracted, a folding shape of the balloon is formed entirely at the straight pipe part and the taper parts such that wing parts 6 and groove parts 7 are alternately formed as shown in FIG. 3. At that time, it is advantageous in passage of the balloon through a narrowed area and operability of the balloon to increase the number of wing parts formed when the balloon is contracted (the number of wing parts is three or more), that is, to shorten the length of the wing parts 6 extended in the radial direction around the catheter shaft and reduce a profile diameter of the balloon when being folded (hereinafter, simply referred to as "profile diameter" unless otherwise stated). In order to reduce the profile diameter, it is important to eliminate excessive unevenness of film thickness in the straight pipe part of the expansion balloon. Therefore, for further improvement of the foregoing passage and operability, it is essential to stably control the folding shape of the balloon almost uniform in film thickness in the circumferential direction, reduce the profile diameter, and keep the profile diameter stable.

To realize the foregoing issue, the present invention employs a production method of a balloon tube for use in blow molding of a balloon by which the tube is configured to have a cross section with the shape (outer peripheral shape) of a circle on the outside and the shape (inner peripheral shape) of a polygon having a circumcircle on the inside, and the balloon tube is subjected to biaxially-stretched blow molding. Specifically, in the present invention, an expansion balloon is produced by performing a step (step 1) of obtaining a balloon tube that has a cross section orthogonal to the axial direction with the shape of a circle on the outside and the shape of a polygon having a circumcircle on the inside, and a step (step 2) of placing the balloon tube in a mold and subjecting the balloon tube to biaxially-stretched blow molding to obtain a balloon.

First, at step 1, a balloon tube that has a cross section orthogonal to the axial direction with the shape of a circle on the outside and the shape of a polygon with a circumcircle on the inside is molded. There is no particular limitation on the inside shape of the balloon tube for use in the present invention, provided that the shape of a polygon is a circumcircle. However, from the viewpoint of ease of making almost uniform the film thickness of the straight pipe part of the balloon, the tube has preferably the inside shape of a regular polygon. In addition, from the same viewpoint, the circumcircle is preferably concentric to the center of the outside circle. As for the "regular polygon" in the present invention, it is not necessarily required that all the inner angles of the polygon are identical in a strict manner and all the sides of the same are identical in length in a strict manner, but slight fluctuations are allowed.

In the following descriptions of embodiments, the inside shape of the balloon tube is a regular polygon. As a matter of the course, various polygons can be employed within the scope of advantages of the present invention.

In addition, there is no particular limitation on the number of angles of the polygon, but the polygon preferably has a specific number of angles as described later.

FIG. 4 is a schematic perspective view of a first embodiment of a balloon tube for use in the present invention. In the embodiment, the cross section of a balloon tube 8a orthogonal to the axial direction has the shape of a circle on the outside and the shape of a regular triangle on the inside. In addition, in this example, the balloon tube 8a has a cross section that has the shape of a circle on the outside 13a and the shape of a regular triangle on the inside 14a over the entire length of the balloon tube 8a in the axial (longitudinal) direction. Further, in the embodiment, apex parts of the regular triangle on the inside are located at the same positions in the axial (longitudinal) direction. Alternatively, the positions of the apex parts of the regular triangle may be continuously changed in the axial direction to, when the tube is turned into a balloon, form the wing parts in a spiral manner, not in parallel to the axial direction of the balloon.

FIG. 5 is a cross-sectional view of FIG. 4 taken along B-B line. As shown in FIG. 5, in the embodiment, the outer peripheral shape of the cross section on the outside 13a is a circle, and the inner peripheral shape of the cross section on the inside 14a is a regular triangle. The regular triangle on the inside 14a is formed such that apex parts 9a contact internally a circumcircle 15a on the inside that is concentric to the center of the circle on the outside 13a. Diameter of the circumcircle 15a can be decided as appropriate taking into account film thickness of the expansion balloon and the like. However, from the viewpoint of producing a balloon almost uniform in film thickness, the ratio of a diameter (R1) of the outside circle to a diameter (R2) of the circumcircle (R1/R2: value obtained by dividing R1 by R2) is preferably 1.3 or more and 2.8 or less.

As a production method for a balloon tube that has the shape of a regular polygon on the inside, for example, an extrusion die (mold) having the shape corresponding to the desired regular-polygonal cross section of the balloon tube can be used for extrusion molding. As another production method, a balloon tube is put on a regular-polygonal core material, a heat-shrinkable tube is put on the balloon tube, and hot wind is applied to the heat-shrinkable tube to contract the balloon tube, thereby to obtain a tube that has the same shape as that of the core material on the inside and has the shape of a circle on the outside. However, the balloon tube is preferably produced by extrusion molding from the viewpoint of simplicity and blow molding yield.

Then, at step 2, the balloon tube 8a is placed in a balloon mold, and the balloon tube 8a is stretched in the axial direction and the radial direction by biaxially-stretched blow molding, thereby to produce the desired expansion balloon. The shape of the cavity of the balloon mold corresponds to the outer shape of the balloon if the balloon is the balloon 2 having the outer shape shown in FIGS. 1 and 2, for example, that is, if the balloon is a balloon that has the straight pipe part 4 with a columnar outer shape, the taper parts 5a and 5b with an almost conical outer shape, and the sleeve parts 12a and 12b with a columnar outer shape. The usable mold has a paired structure that can be opened and closed, for example, such that the paired molds are each provided with a concave portion so that, when being closed, the molds have the shape corresponding to the outer shape of the balloon.

There is no particular limitation on the expansion rate of the balloon during blow molding (inner diameter of the balloon mold/inner diameter of the balloon tube: value obtained by dividing the inner diameter of the balloon mold by the inner diameter of the balloon tube). However, the expansion rate is preferably 4 or more and more preferably 6 or less, at a section corresponding to the straight pipe part of the balloon, from the viewpoint of making almost uniform film thickness of the straight pipe part of the balloon. In addition, the expansion rate is preferably 9 or less and more preferably 8 or less, from the viewpoint of performing stable blow molding. The "inner diameter of the balloon mold" here refers to the inner diameter of the cavity corresponding to the straight pipe part of the balloon, and the "inner diameter of the balloon tube" here refers to, in the case of a regular polygon, a circumcircle of the regular polygon.

Biaxial stretching may be performed under heat condition and may be performed more than once. In addition, axial stretching may be performed concurrently with radial stretching or may be performed before or after the radial stretching.

In the thus obtained expansion balloon, since the balloon tube having the cross section with the shape of a circle on the outside and the shape of a polygon on the inside is subjected to biaxial stretching, the straight pipe part has the shape of an almost circle on the inside and has an almost uniform film thickness in the circumferential direction. The term "almost uniform" in the present invention means that a variation coefficient (standard deviation/average value) is 6.0% or less. This level of variation coefficient exerts no influence on the profile diameter of the balloon when being folded, thereby making it possible to maintain the stable profile diameter.

After the biaxially-stretched blow molding, the expansion balloon may be subjected to an annealing process to stabilize the shape and dimensions of the expansion balloon.

In the balloon catheter assembled using the expansion balloon produced from the balloon tube 8a shown in FIG. 4 or 5(*a*), when the expansion balloon is expanded and then contracted, a folding shape of the balloon is formed such that the apex parts 9a of the regular triangle shrink to the wing parts and the side parts 10a of the same shrink to a circumcenter (in FIG. 3, for example, outer surface of the catheter shaft 3b) to form groove parts, and the wing parts and the groove parts extend in the longitudinal direction of the balloon. The apex parts 9a form the wing parts and the side parts 10a form the groove parts because, when the balloon tube inflates in the radial direction during blow molding, the foregoing expansion rate on blow molding is different between the apex parts 9a and the side parts 10a. In general, when the expansion rate on blow molding is changed, the balloon strength and the balloon stretch characteristics vary to exert large influence on the balloon physical properties (molecular orientation, crystallinity degree, and the like). Therefore, the apex parts can form the wing parts and the side parts can form the groove parts due to variations in balloon physical properties resulting from a difference in the expansion rate. For example, when the balloon tube 8a having the cross-sectional shape shown in FIG. 5(*a*) is produced by blow molding, the cross-sectional structure of the straight pipe part of the obtained expansion balloon is configured such that the cross-sectional parts of the balloon corresponding to the apex parts 9a and the side parts 10a shown in FIG. 5(*a*) constitute cross-sectional parts different in physical properties shown by reference numerals 16 and 17, respectively, in the schematic view of FIG. 5(*b*). In addition, the cross-sectional parts are alternately formed in the circumferential direction of the balloon and are continuously extended in the longitudinal direction of the balloon, and thus when the balloon is contracted, the wing parts 6 shown in FIG. 3 are prone to be formed at the parts with reference numeral 16 in FIG. 5(*b*) and the groove parts 7 are prone to be formed at the parts with reference numeral 17 in FIG. 5(*b*).

FIGS. 6 to 8 show cross sections of balloon tubes orthogonal to the axial direction in second to fourth embodiments for use in the present invention, respectively. Although not shown, as in the perspective view of FIG. 4 of the first embodiment, the balloon tubes 8b, 8c, and 8d have cross sections that have the shape of a circle on the outside and the shapes of a regular tetragon, a regular hexagon, and a regular octagon on the inside, respectively, over the entire length of the balloon tubes in the axial (longitudinal) direction. In addition, as in the case of the first embodiment, the positions of the apex parts of the regular polygons may be continuously changed in the axial direction. When the balloon tubes 8b, 8c, and 8d in the second to fourth embodiments are subjected to blow molding, as in the case of the first embodiment, the cross-sectional structures of the straight pipe parts of the obtained expansion balloons are configured such that the cross-sectional parts of the balloons corresponding to the apex parts 9b, 9c, and 9d and the side parts 10b, 10c, and 10d are alternately formed in the circumferential direction of the balloon, and these parts are extended continuously in the longitudinal direction of the balloons, and when balloons are contracted, the wing parts are formed at parts corresponding to the apex parts 9b, 9c, and 9d, and groove parts are formed at parts corresponding to the side parts 10b, 10c, and 10d.

As shown in FIGS. 6, 7, and 8, the balloon tubes 8b, 8c, and 8d that have the cross sections having the shape of a circle on the outsides 13b, 13c, and 13d and having the shapes of a regular tetragon, a regular hexagon, and a regular octagon on the insides 14b, 14c, and 14d can be produced as in the case of the first embodiment shown in FIG. 4 or 5(*a*), by using extrusion dies having the shapes corresponding to the desired cross sections of the regular-polygonal balloon tubes. In addition, these balloon tubes can also be subjected to biaxially-stretched blow molding as in the case of the first embodiment.

When the expansion balloons produced from these balloon tubes are folded, the numbers of wing parts formed vary according to the inside shapes such that three is in the case of a regular triangle, four is in the case of a regular tetragon, three is in the case of a regular hexagon, and four is in the case of a regular octagon, and in the case of polygons with six or more apex parts, there is a tendency that no wing parts identical in number to the apex parts can be obtained. If the sizes of circles formed in the circumcircles of the regular polygons (refer to the parts with reference numerals 15a, 15b, 15c, and 15d in FIGS. 5(a) and 6 to 8) are unified, as the number of apex parts becomes larger as with the regular hexagon and the regular octagon, the length of the side parts linking the apex parts becomes shorter, which makes it difficult to form the groove parts. Accordingly, when two adjacent apex parts are going to form wing parts, one of the apex parts is taken into the other to form one wing part.

Therefore, a regular hexagon and a regular octagon provide a number of folds in multiples of 3 or 4, which allows stable folding control, whereas regular polygons not in multiples of 3 or 4 such as a regular pentagon and a regular heptagon, there is a tendency that stable folding control is difficult. Accordingly, in the present invention, the inside of the cross section of the balloon tube orthogonal to the axial direction is preferably formed by a regular polygon in multiples of 3 or 4. From the viewpoint of reducing the length of the wing parts extending in the radial direction, the number of angles of the regular polygon is preferably four or more.

The number of wing parts of a regular enneagon is three. This is because two apex parts exist between the wing parts, and not only one of adjacent wing parts but also a wing part next to the adjacent wing parts are taken to form one wing part or apex parts on both sides of an apex part constituting the wing part are taken to form one wing part. If the number of angles of the regular polygon becomes large, the balloon tube is folded in such a manner described above with variations in dimensions of the respective wing parts, and thus there is a tendency that it is difficult to stabilize the profile diameter. Thus, from the viewpoint of stabilizing the profile diameter, the number of angles of the regular polygon on the inside of the cross section is preferably eight or less.

From the foregoing viewpoints, the inside of the cross section of the balloon tube orthogonal to the axial direction more preferably has the shape of a regular tetragon, a regular hexagon, or a regular octagon.

The expansion balloon produced by the production method of the present invention is used to expand a narrowed area in a blood vessel by percutaneous luminal surgery including peripheral angioplasty, coronary artery angioplasty, and valvuloplasty. At the percutaneous luminal surgery, a balloon catheter is inserted from outside the body and the balloon is advanced to a treatment site, and then the balloon is inflated to expand the narrowed area to restore a blood flow. To remove the catheter from the body or advance the catheter again to another lesion area, it is advantageous to make small the folding diameter (profile diameter) when the expanded balloon is contracted again.

EXAMPLES

Specific examples and comparative examples of production method for an expansion balloon according to the present invention will be described below in detail. The present invention is not limited to the following examples. Table 1 provides details of specifications for balloon tubes and balloons.

Example 1

A balloon tube was produced by extrusion molding so as to have a tube cross section with the shape of a circle on the outside and the shape of a regular triangle on the inside as shown in FIG. 4 or 5(a), by using polyamide elastomer with a durometer hardness of 72D (trade name: PEBAX7233SA01: produced by Arkema KK). Tube dimensions were designed such that the outer diameter of the tube was 0.98 mm, the diameter of a circumcircle (15a) of the regular polygon constituting the inside of the tube was 0.44 mm, and the outside circle and the circumcircle (15a) were concentric to each other. Then, the extrusion-molded balloon tube was set into a balloon mold (the inner diameter of the cavity corresponding to the straight pipe part is 3.00 mm) to subject the balloon tube to biaxially-stretched blow molding such that the expansion rate becomes 6.8, thereby producing five expansion balloons in which the diameter of the straight pipe part was 3.00 mm, the length of the straight pipe part was 15 mm, and the lengths of the taper parts at the distal side and the proximal side were both 4 mm.

Example 2

A balloon tube was produced by using the same material as that of Example 1 and with the same dimensions as those of Example 1 (outer diameter and diameter of the circumcircle (15b)) so as to have a cross section with the shape of a circle on the outside and the shape of a regular tetragon on the inside as shown in FIG. 6. Then, five balloons with the same shape as that of Example 1 were produced by the same method as that for Example 1.

Example 3

A balloon tube was produced by using the same material as that of Example 1 and with the same dimensions as those of Example 1 (outer diameter and diameter of the circumcircle (15c)) so as to have a cross section with the shape of a circle on the outside and the shape of a regular hexagon on the inside as shown in FIG. 7. Then, five balloons with the same shape as that of Example 1 were produced by the same method as that for Example 1.

Example 4

A balloon tube was produced by using the same material as that of Example 1 and with the same dimensions as those of Example 1 (outer diameter and diameter of the circumcircle (15d)) so as to have a cross section with the shape of a circle on the outside and the shape of a regular octagon on the inside as shown in FIG. 8. Then, five balloons with the same shape as that of Example 1 were produced by the same method as that for Example 1.

Comparative Example 1

A balloon tube (not shown) was produced by using the same material as that of Example 1 and with the same dimensions (outer diameter) as those of Example 1 so as to have a cross section with the shape of a circle both on the outside and the inside. Then, five balloons were produced by the same method as that for Example 1. The diameters of the circumcircles in the examples and the diameter of the inside circle of Comparative Example 1 were the same.
(Evaluation)

The expansion balloons produced as the examples and the comparative example were expanded for 30 minutes in the water at 37° C. under 1.82 Mpa. After that, the balloons were contracted and the numbers of wing parts formed at folding of the balloons were counted. In addition, film thicknesses of the straight pipe parts of the balloons in the examples were measured at the middle portion and both ends by a micrometer at intervals of 60° in the circumferential direction, and thus the film thicknesses were determined at 18 points. At that time, the thicknesses of the entire balloons were evenly measured with measurement position shifts by 10 to 20° such that the (total three) measurement points at the middle portion and the both ends did not align in a straight line.
(Evaluation Results)

Referring to Table 1, the number of wing parts formed at folding of the balloon was three in Examples 1 and 3 and the number of the same was four in Examples 2 and 4, whereas the number of the same was two in the comparative example. Thus, it has been found that the profile diameter could be reduced in all of the examples. In addition, the numbers of wing parts were the same in all of the (five) samples produced as each of the examples, and thus it has been revealed that the folding shapes were stable in all of the examples. Further, it has also been revealed that the balloon film thicknesses in the examples were at the same level as the comparative example. Moreover, in all of the examples according to the present invention, a series of molding processes was simple and molding yields were high significantly.

15a, 15b, 15c, 15d Circumcircle
16 Balloon cross-sectional part corresponding to apex part
17 Balloon cross-sectional part corresponding to side part

The invention claimed is:

1. A production method for an expansion balloon for use in a balloon catheter, comprising the steps of:
    obtaining a balloon tube that has a cross section orthogonal to an axial direction with the shape of a circle on the outside and the shape of a polygon having a circumcircle on the inside, said polygon having a plurality of sides and a plurality of apices; and
    subjecting the balloon tube to biaxially-stretched blow molding in a mold for biaxially-stretched blow molding to obtain the balloon,
    wherein the balloon has a straight pipe part and film thickness of the straight pipe part is almost uniform,
    wherein the straight pipe part has an inside and an outside both having a circle-shaped cross section orthogonal to an axial direction, and
    wherein the balloon formed by biaxially-stretched blow molding has a region corresponding to each of said plurality of apices that has properties that different from regions corresponding to each of said plurality of slides.

2. The production method for an expansion balloon according to claim 1, wherein the balloon tube has the cross section with the shape of a polygon having a circumcircle in multiples of 3 or 4 on the inside.

3. The production method for an expansion balloon according to claim 1 or 2, wherein the balloon tube has the

TABLE 1

| | Tube cross sectional shape | | Balloon straight pipe part film thickness | | Number of wing parts in contracted balloon (units) | Number of folds (units/total units) |
| --- | --- | --- | --- | --- | --- | --- |
| | Outside | Inside | Average value ± standard deviation (μm) | Variation coefficient (%) | | |
| Example 1 | Circle | Regular triangle | 24.5 ± 1.4 | 5.7 | 3 | 5/5 |
| Example 2 | Circle | Regular tetragon | 24.3 ± 1.2 | 4.9 | 4 | 5/5 |
| Example 3 | Circle | Regular hexagon | 24.0 ± 0.7 | 2.9 | 3 | 5/5 |
| Example 4 | Circle | Regular octagon | 23.8 ± 0.9 | 3.8 | 4 | 5/5 |
| Comparative Example 1 | Circle | Circle | 24.5 ± 1.5 | 6.1 | 2 | 5/5 |

REFERENCE SIGNS LIST

1 Balloon catheter
2 Expansion balloon
3 Catheter shaft
3a Outer pipe
3b Inner pipe
4 Balloon straight pipe part
5 Balloon taper part
6 Wing part
7 Groove part
8 Balloon tube
9a, 9b, 9c, 9d Apex part
10a, 10b, 10c, 10d Side part
11 Hub
12 Sleeve part
13a, 13b, 13c, 13d Outside
14a, 14b, 14c, 14d Inside cross section with the shape of a polygon having any circumcircle selected from among a tetragon, a hexagon, and an octagon on the inside.

4. The production method for an expansion balloon according to claim 1, wherein the polygon having a circumcircle is a regular polygon.

5. The production method for an expansion balloon according to claim 1, wherein the outside shape and inside shape of the cross section of the balloon tube are formed over the entire length in the axial direction.

6. The production method for an expansion balloon according to claim 1, wherein expansion rate of the balloon under the biaxially-stretched blow molding is 4 or more and 9 or less.

* * * * *